United States Patent
Connelly et al.

(10) Patent No.: US 6,722,364 B2
(45) Date of Patent: Apr. 20, 2004

(54) MEDICAMENT INHALATION DELIVERY DEVICES AND METHODS FOR USING THE SAME

(75) Inventors: Robert I. Connelly, Raleigh, NC (US); Vincent J. Sullivan, Morrisville, NC (US); Charles D. Shermer, Raleigh, NC (US); Anjana Bhuta, Cary, NC (US); Ronald J. Pettis, Durham, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 32 days.

(21) Appl. No.: 09/758,776

(22) Filed: Jan. 12, 2001

(65) Prior Publication Data
US 2002/0092523 A1 Jul. 18, 2002

(51) Int. Cl.[7] .................. A61M 15/00; A61M 16/00
(52) U.S. Cl. .................. 128/203.15; 128/200.23; 128/203.12; 128/203.21
(58) Field of Search .......... 128/203.15, 203.21, 128/203.12, 203.14, 205.21, 200.23; 604/58, 415; 206/528, 531, 532; 239/338

(56) References Cited

U.S. PATENT DOCUMENTS

| | | |
|---|---|---|
| 3,625,213 A | 12/1971 | Brown |
| 3,949,751 A * | 4/1976 | Birch et al. ............. 128/203.15 |
| 4,344,573 A | 8/1982 | De Felice |
| 4,723,691 A | 2/1988 | Minkevitch et al. |
| 4,900,315 A | 2/1990 | Lundqvist et al. |
| 4,962,868 A | 10/1990 | Borchard |
| 5,215,221 A | 6/1993 | Dirksing |
| 5,239,991 A | 8/1993 | Chawla et al. |
| 5,307,953 A | 5/1994 | Regan |
| 5,331,954 A | 7/1994 | Rex et al. |
| 5,349,947 A | 9/1994 | Newhouse et al. |
| 5,513,630 A | 5/1996 | Century |
| 5,533,505 A | 7/1996 | Kallstrand et al. |
| 5,542,412 A | 8/1996 | Century |
| 5,547,131 A | 8/1996 | Brace |
| 5,601,077 A | 2/1997 | Imbert |
| 5,702,362 A | 12/1997 | Herold et al. |
| 5,797,392 A | 8/1998 | Keldmann et al. |
| 5,819,730 A | 10/1998 | Stone et al. |
| 5,881,716 A * | 3/1999 | Wirch et al. ............. 128/200.14 |
| 5,881,719 A | 3/1999 | Gottenauer et al. |
| 5,881,720 A | 3/1999 | Vinogradov et al. |
| 5,894,967 A | 4/1999 | Stahley et al. |
| 5,918,594 A * | 7/1999 | Asking et al. ............. 128/203.12 |
| 5,941,867 A * | 8/1999 | Kao ............................. 604/403 |
| 6,065,472 A * | 5/2000 | Anderson et al. ......... 128/200.18 |
| 6,105,574 A * | 8/2000 | Jahnsson ................ 128/203.15 |
| 6,308,704 B1 * | 10/2001 | Wennerberg ............ 128/203.12 |

FOREIGN PATENT DOCUMENTS

| | | |
|---|---|---|
| WO | WO 92/05824 | 4/1992 |
| WO | WO 92/06727 | 4/1992 |
| WO | WO 97/10017 | 3/1997 |
| WO | WO 97/25087 | 7/1997 |
| WO | WO 97/40876 | 11/1997 |
| WO | WO 99/47099 | 9/1999 |
| WO | WO 99/56807 | 11/1999 |

* cited by examiner

Primary Examiner—Weilun Lo
Assistant Examiner—Darwin P Erezo
(74) Attorney, Agent, or Firm—David M. Fortunato; Robert E. West; Ludomir A. Budzyn

(57) ABSTRACT

A medicament delivery device for administering a medicament to a user includes a medicament reservoir and an entrance port and an exit port each disposed adjacent the reservoir. A gas chamber disposed adjacent the entrance port. The device includes a pressurizing mechanism operable to pressurize said gas chamber to at least a prescribed pressure. A first frangible membrane extends across the entrance port and separates the reservoir from the gas chamber. A second frangible membrane extends across the exit port. When the pressurizing mechanism is attached, at least one of the first and second membranes is responsive to the prescribed pressure in the gas chamber to burst to allow gas to flow through the entrance port and the reservoir and to carry the medicament through the exit port.

47 Claims, 11 Drawing Sheets

MEDICAMENT INHALATION DELIVERY DEVICES AND METHODS FOR USING THE SAME

FIELD OF THE INVENTION

The present invention relates to medicament delivery devices and, more particularly, to devices for administering inhalable medicaments.

BACKGROUND OF THE INVENTION

Inhalers are commonly used to deliver various medicaments to users via the user's nose or mouth. Such medicaments increasingly include dry powders. A number of considerations affecting the efficacy of delivery may be presented, particularly in the case of dry powders. For example, it may be important to ensure that the appropriate dose is metered and expressed, that the medicament is properly dispersed in the conveying fluid (e.g., the carrier gas), that the delivery device is not unduly susceptible to user error in operation, and/or that undue inhalation strength is not required. Further considerations may include the operating complexity, portability and size of the delivery device. Because inhalation therapy often requires numerous applications, the cost of providing the dosage may be of particular importance.

SUMMARY OF THE INVENTION

According to embodiments of the present invention, a medicament delivery device for administering a medicament to a user includes a medicament reservoir and an entrance port and an exit port each disposed adjacent the reservoir. A gas chamber is disposed adjacent the entrance port. The device includes a pressurizing mechanism operable to pressurize the gas chamber to at least a prescribed pressure. A first frangible membrane extends across the entrance port and separates the reservoir from the gas chamber. A second frangible membrane extends across the exit port. When the pressurizing mechanism is attached, at least one of the first and second membranes is responsive to the prescribed pressure in the gas chamber to burst to allow gas to flow through the entrance port and the reservoir and to carry the medicament through the exit port.

The pressurizing mechanism may include a compressible blister defining the gas chamber and operable to pressurize the gas chamber to at least the prescribed pressure. The device may include: a first sheet including the compressible blister formed therein; a second sheet defining the reservoir therein; and an intermediate layer disposed between the first and second sheets, the first and second membranes forming a part of the intermediate layer.

According to further embodiments of the present invention, a medicament delivery device for administering a medicament to a user includes a medicament reservoir and an entrance port and an exit port each disposed adjacent the reservoir. The device includes a compressible blister defining a gas chamber and operable to pressurize the gas chamber to at least a prescribed pressure. A frangible membrane extends across the entrance port and separates the reservoir from the gas chamber. When the blister is compressed, the membrane is responsive to the prescribed pressure in the gas chamber to burst to allow gas to flow through the entrance port and the reservoir and to carry the medicament through the exit port.

According to further embodiments of the present invention, a method for administering a medicament to a user includes providing a medicament delivery device including: a medicament reservoir; an entrance port and an exit port each disposed adjacent the reservoir; a gas chamber disposed adjacent the entrance port; a pressurizing mechanism operable to pressurize the gas chamber to at least a prescribed pressure; a first frangible membrane extending across the entrance port and separating the reservoir from the gas chamber; and a second frangible membrane extending across the exit port. The pressurizing mechanism is actuated to generate the prescribed pressure in the gas chamber, whereupon at least one of the first and second membranes bursts to allow gas to flow through the entrance port and the reservoir and to carry the medicament through the exit port.

According to further embodiments of the present invention, a method for administering a medicament to a user includes providing a medicament delivery device including: a medicament reservoir; an entrance port and an exit port each disposed adjacent the reservoir; a compressible blister defining a gas chamber and operable to pressurize the gas chamber to at least a prescribed pressure; and a frangible membrane extending across the entrance port and separating the reservoir from the gas chamber. The blister is compressed to generate the prescribed pressure in the gas chamber, whereupon the frangible membrane bursts to allow gas to flow through the entrance port and the reservoir and to carry the medicament through the exit port.

Objects of the present invention will be appreciated by those of ordinary skill in the art from a reading of the figures and the detailed description of the preferred embodiments which follow, such description being merely illustrative of the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF THE PREFERRED EMBODIMENTS

Figure 1:
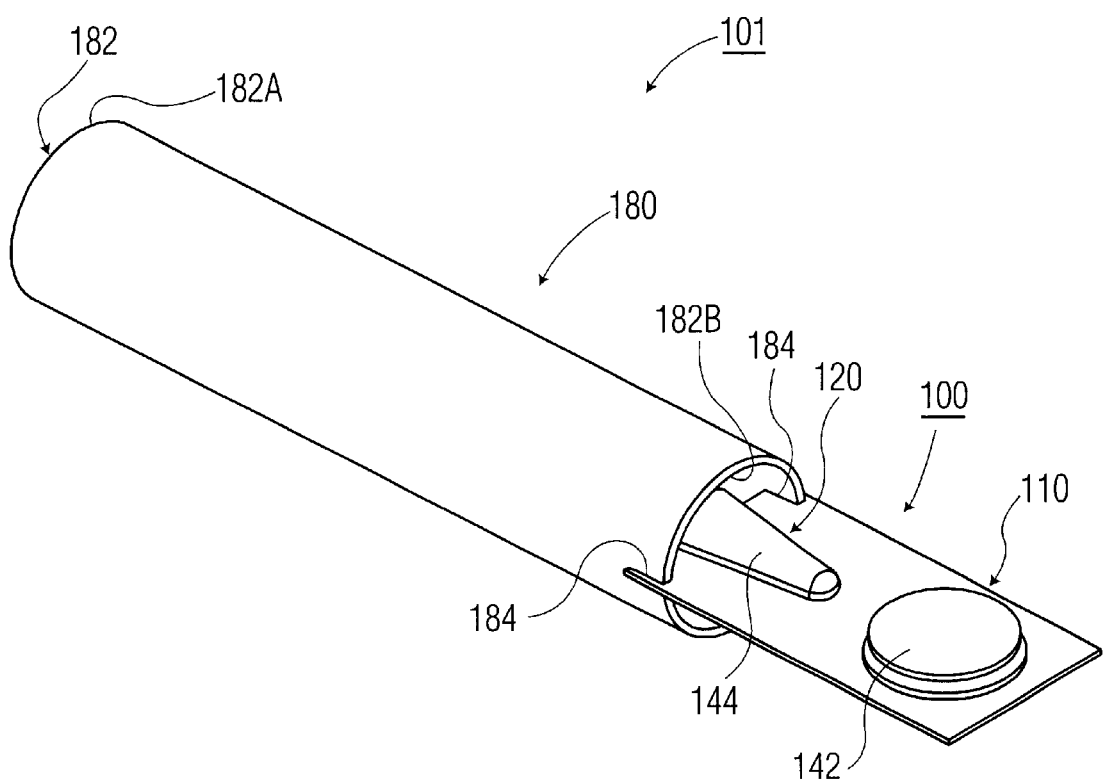
FIG. 1 is a perspective view of a delivery device according to embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain components and the thicknesses of some layers may be exaggerated for clarity.

With reference to FIGS. 1–4, a medicament inhalation delivery device 101 according to embodiments of the present invention is shown therein. The delivery device 101 includes a dispenser 100 and a delivery tube 180 (see FIG. 1). The dispenser 100 includes a pressurizing mechanism 110, a storage volume 116 and a diffuser tube 120. The dispenser 100 contains a quantity of a desired medicament 5 (see FIG. 3) in the storage volume 116. Preferably, the quantity of medicament corresponds to a single therapeutic dose. The medicament 5 may be a sterile, dry powder medicament.

Generally, and as discussed in greater detail below, the medicament 5 may be delivered to the airway of the user, typically to the mouth or nose of the user by locating the free end of the delivery tube 180 adjacent the user's mouth or nose and actuating the pressurizing mechanism 110. In this manner, a carrier gas 111 is forced through the storage volume 116, the diffuser tube 120 and the delivery tube 180. As the carrier gas 111 flows through the storage volume 116, the medicament 5 becomes entrained in the gas 111 and is transported and expelled from the delivery tube with the gas to the user. Optionally, the delivery tube 180 may be omitted, in which case the open end of the diffuser tube 120 may be directly located adjacent the mouth or nose of the user.

Figure 2:
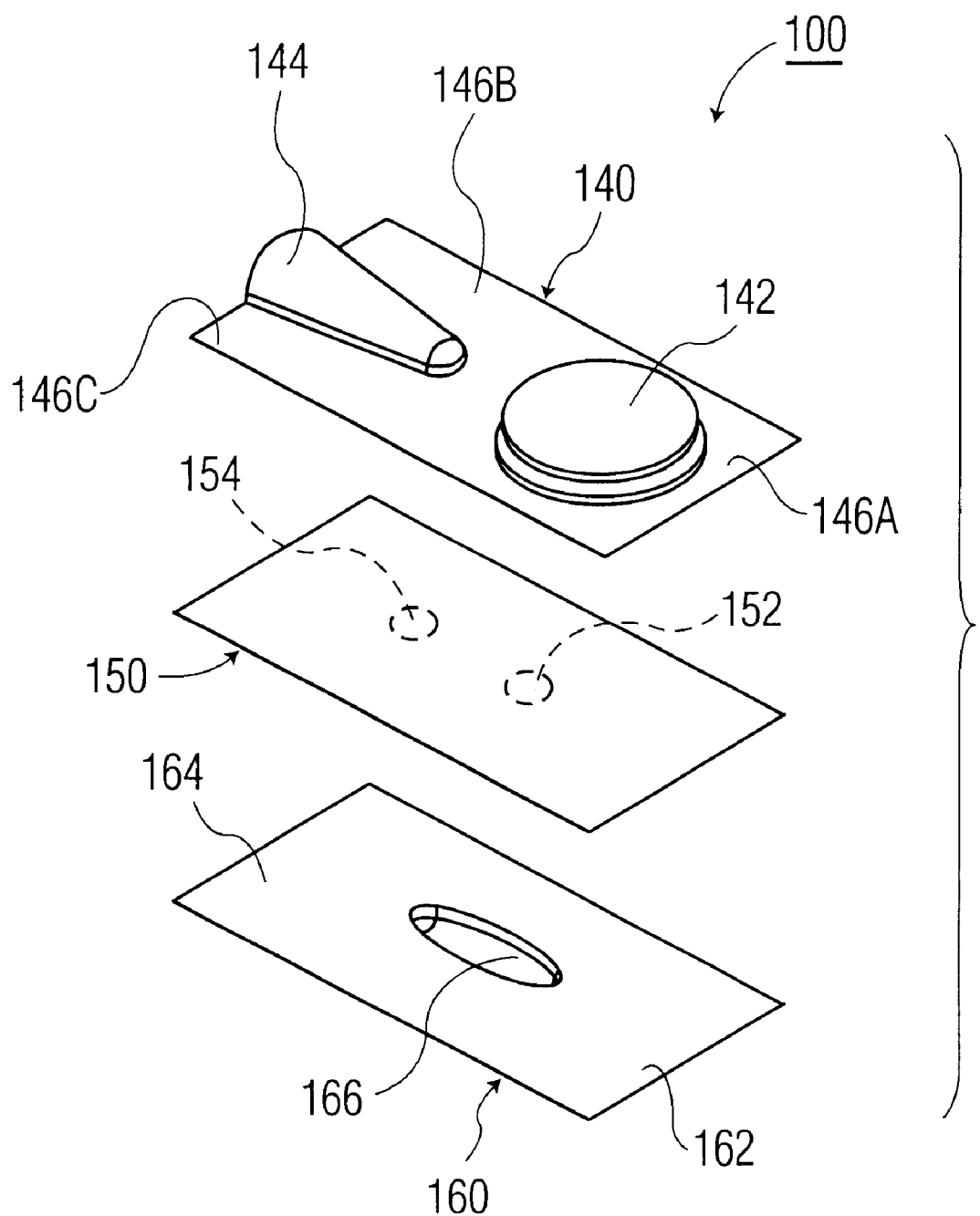
FIG. 2 is an exploded, perspective view of a dispenser forming a part of the delivery device of FIG. 1.
Figure 3:
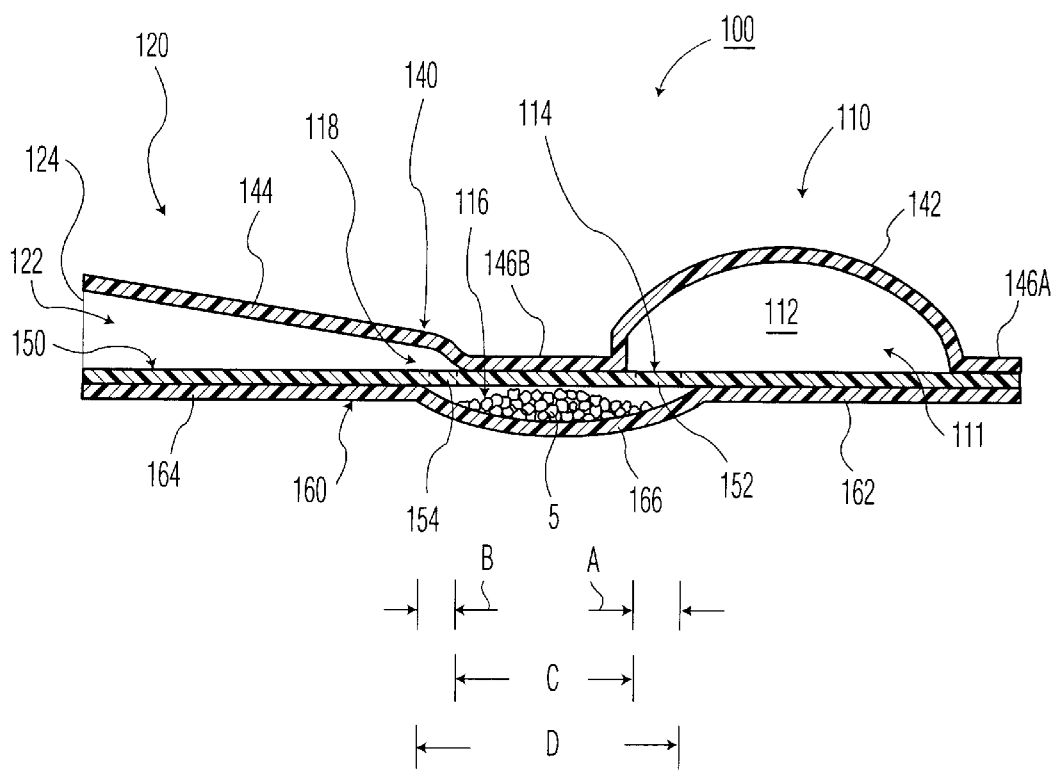
FIG. 3 is a center cross-sectional view of the dispenser of FIG. 2.

As best seen in FIGS. 2 and 3, the dispenser 100 includes an upper sheet 140, a lower sheet 160 and an intermediate sheet 150. The relative thickness of the intermediate sheet 150 is exaggerated in FIGS. 3 and 4 for clarity. The upper sheet has a blister 142 and a cone-shaped channel 144 formed therein. The blister 142 and the channel 144 are surrounded by marginal portions 146A, 146B and 146C (FIG. 3). The lower sheet 160 has a reservoir 166 formed therein and marginal portions 162, 164 surrounding the reservoir 166.

The sheets 140, 150, 160 are relatively configured and disposed such that the upper sheet 140 is joined to the intermediate sheet 150, and thereby to the lower sheet 160, by the marginal portions 146A and 146C (see FIG. 2). While the intermediate sheet 150 is shown as extending the full length of the dispenser 100, the intermediate sheet 150 may be abbreviated and may comprise multiple, discrete sheets. For example, one such sheet may include the membrane 152 as described below and another, separate such sheet may include the membrane 154 as described below.

A central portion 146B of the upper sheet 140 is laminated to the intermediate sheet 150 and overlies the reservoir 166. The length D of the reservoir 166 is greater than the length C of the central portion 146B so that an entrance opening or port 114 and an exit opening or port 118 are defined on either side of the central portion 146B. The ports 114 and 118 have lengths A and B, respectively. The intermediate sheet 150 includes a first or entrance membrane 152 (indicated by dashed lines in FIG. 2) which extends fully across the port 114. The intermediate sheet 150 also includes an exit membrane 154 (indicated by dashed lines in FIG. 2) which extends fully across the port 118. In this manner, the reservoir 166, the entrance membrane 152, the exit membrane 154 and the central portion 146B define the reservoir 166 within which the medicament 5 is fully encapsulated in the storage volume 116.

The blister 142 and the marginal portion 162 form the pressurizing mechanism 110 and define a gas chamber 112. The gas chamber 112 is disposed immediately adjacent the port 114 and is fully sealed from the storage volume 116 by the entrance membrane 152. Similarly, the channel 144 and the marginal portion 164 form the diffuser tube 120 and define a passage 122 and a delivery opening 124. The passage 122 is disposed immediately adjacent the port 118 and is fully sealed from the storage volume 116 by the exit membrane 154.

The upper and lower sheets 140, 160 are preferably thermoformed from a suitable polymeric or elastomeric material. More preferably, the upper and lower sheets 140, 160 are formed of a co-laminated or co-extruded film including a layer of thermoformable polyethylene terephthalate (PET) on the exterior thereof and a layer of heat-sealable polyethylene on the interior thereof. The intermediate layer 150 is preferably formed of a layer of polyethylene. Preferably, the intermediate layer 150 has a thickness of between about ½ and 4 mil. Preferably, the intermediate layer 150 has a burst pressure of between about 4.4 and 89.0 Newtons. Preferably, the intermediate layer 150 has a tensile strength of between about 10 and 50 MPascals.

The gas chamber 112 preferably has a volume of between about 0.2 and 10 milliliters. The gas in the gas chamber 112 and the gas in the storage volume 116 can be the same or different gases. These gases may be air or other suitable gases. For example, noble gases, $N_2$, Ar or He may be used.

The medicament 5 may be any substance which produces a clinically useful result. By "clinically useful result" is meant clinically adequate prevention or treatment of a disease or condition by administration of a substance. Examples include, but are not limited to, clinically adequate control of blood sugar levels (insulin), clinically adequate management of hormone deficiency (PTH, Growth Hormone, etc.), expression of protective immunity (vaccines), prevention of thrombosis (heparin or derivatives), alleviation or prevention of pain (antimigraines, opiods, etc.), infection control (antibiotics), allergy control, or clinically adequate treatment of toxicity (antitoxins). More preferably, the medicament 5 is a dry powder consisting of a substance producing a clinically useful result. Such substances may be incorporated as components of mixtures with other excipients by processes which are known in the art. Such processes may include, but are not limited to, freeze drying of mixtures followed by dry blending, spray drying and supercritical processing methods.

The dispenser 100 (or a series of dispensers 100) may be formed on a web in a manner similar to that commonly employed to form blister packs. The blister 142 and the channel 144 are thermoformed in a web corresponding to the upper sheet 140, and the reservoir 166 is thermoformed in a web corresponding to the lower sheet 160. A web corresponding to the intermediate sheet 150 is inserted between the webs corresponding to the sheets 140 and 160. The webs corresponding to the sheets 140, 150 and 160 are then heat sealed in the layered configuration as shown in FIG. 3 with the medicament 5 disposed in the reservoir 160. Preferably, the medicament 5 is first placed in the reservoir 166, the web corresponding to the sheet 150 is thereafter heat sealed to the web corresponding to the sheet 160 to package the medicament 5, and the web corresponding to the sheet 140 is thereafter heat sealed to the opposite side of the web corresponding to the sheet 150 to form a unitary dispenser 100. The dispenser 100 is then die cut or otherwise severed from the remainder of the webs.

For inhalation through the nose, the dispenser 100 is preferably used without the delivery tube 180. For inhalation through the mouth, the dispenser 100 may be mounted in the opening 182B of the delivery tube 180 by means of slots 184 (FIG. 1). The delivery opening 182A of the delivery tube 180 is placed adjacent the user's mouth or, alternatively, the delivery opening 124 of the diffuser tube 120 is placed adjacent the user's nose. Preferably, in operation, the dispenser 100 is oriented such that the blister 142 is on top and the reservoir 166 is on bottom.

Figure 4:
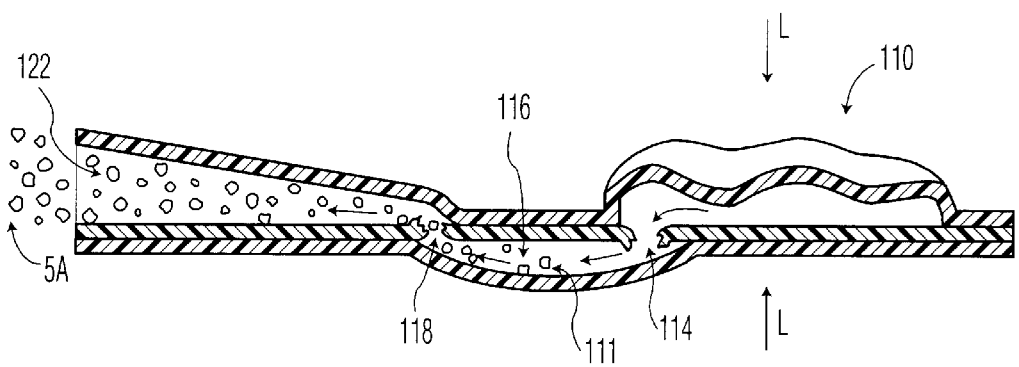
FIG. 4 is a center cross-sectional view of the dispenser of FIG. 2 wherein the dispenser is in a partially actuated position.

The user then begins inhaling through the delivery tube 180 or the diffuser tube 120. As the user is inhaling, the user applies a compressive load to the blister 142 as indicated by the direction arrows L in FIG. 4. This may be conveniently and effectively accomplished by squeezing or depressing the blister 142 and the marginal portion 162 between the user's thumb and one or more fingers. As the user compresses the blister 142, the pressure within the gas chamber 112 is increased, thereby applying an increasing load to the entrance membrane 152. When a prescribed pressure is created in the gas chamber 112, the entrance membrane 152 will burst, placing the gas chamber 112 in fluid communication with the storage volume 116. The exit membrane 154 is substantially immediately thereafter loaded by the same pressure and bursts as well, placing the storage volume 116 in fluid communication with the passage 122. As a result, a continuous flow path is provided from the gas chamber 112 to the delivery opening 124. The gas 111 originally in the gas chamber 112 is displaced at high velocity through the ports 114, 118 and the storage volume 116 such that the gas 111 aerosolizes the medicament 5 and a plume 5A including the medicament 5 is forced out of or expelled from the dispenser 100 as shown in FIG. 4. The diffuser tube 120 and/or the delivery tube 180 enable expansion and mixing of the plume and also allow the plume 5A to slow before ultimate delivery to the user.

It will be appreciated that the carrier gas 111 which aerosolizes the medicament may include some or all of the gas stored in the storage volume 116. Moreover, dispensers according to the present invention may be configured such that the gas originally stored in the gas chamber 112 does not ultimately form a part of the plume 5A, but rather this gas displaces a downstream quantity of gas which aerosolizes the medicament 5. Means other than the thermoformed reservoir 166 may be employed to hold the medicament 5 in the flow path of the gas. For example, the reservoir may be separately formed from the pressurizing mechanism 110 or the diffuser tube 120, for example.

The delivery device 101 and the dispenser 100 provide a number of advantages. The dispenser 100 is cost effective to manufacture and may correspond to the cost of simply packaging single doses of the medicament 5 itself.

The delivery device 101 and the dispenser 100 are easy to use. The dispenser 100 can provide a single, accurately measured dose. Because of the provision of the pressurizing mechanism 110, the dispenser 100 does not require a high degree of inspiratory effort on the part of the user to deliver the full, prescribed dose. The dispenser 100 may be disposable, so that no cleaning or reloading is required.

The preferred properties of the membranes 152, 154 and the configurations and dimensions of the blister 142 and the reservoir 166 will depend on the amount and characteristics of the medicament 5, as well as the operational characteristics desired. The prescribed pressure should be high enough to create a sufficient carrier gas velocity to dispense and deaggregate the medicament 5 to thereby create a cloud of the medicament 5 which is suitable for inhalation and which can propel substantially all of the medicament 5. A residue of the medicament 5 may remain in the reservoir 166 after application. Preferably, the amount of residue is no more than 10% of the original amount of medicament 5. However, the prescribed pressure is preferably sufficiently low as to not require undue effort from the user to generate the prescribed pressure in the gas chamber 112.

The prescribed pressure of the dispenser 100 necessary to deliver the medicament 5 will depend on the effective burst pressure and tensile strength of one or both of the membranes 152 and 154. The performance of the dispenser 100 may be varied by appropriately selecting and configuring the materials of the membranes to provide the effective burst pressures and tensile strengths of the membranes 152 and 154.

For some applications, it may be desirable to provide both of the membranes 152 and 154 with substantially the same effective burst pressures and/or tensile strengths. This may be accomplished by forming the membranes 152 and 154 of the same material and with the same dimensions.

For some applications, it may be desirable to provide one of the membranes 152, 154 with a higher effective burst pressure and/or tensile strength than the other membrane 152, 154. It has been found that a more complete emitted dose (i.e., less residual medicament remaining in the reservoir 166 following activation) may be achieved when one of the membranes 152, 154 ruptures at a pressure significantly below the prescribed pressure. In particular, it has been found that for some embodiments the residual dose is substantially reduced or effectively eliminated when the entrance membrane 152 is adapted to burst at a pressure less than the pressure required to burst the exit membrane 154. Preferably, the entrance membrane 152 is adapted to burst at between about 20 and 80% of the pressure at which the exit membrane 154 bursts.

The membranes 152, 154 may be adapted to burst at different pressures by appropriate selection of the relative materials, thicknesses and/or different sizes of ports 114, 118. Alternatively or additionally, the following features may be used to provide differential bursting pressures. These features may be used individually or in combination.

Figure 5:
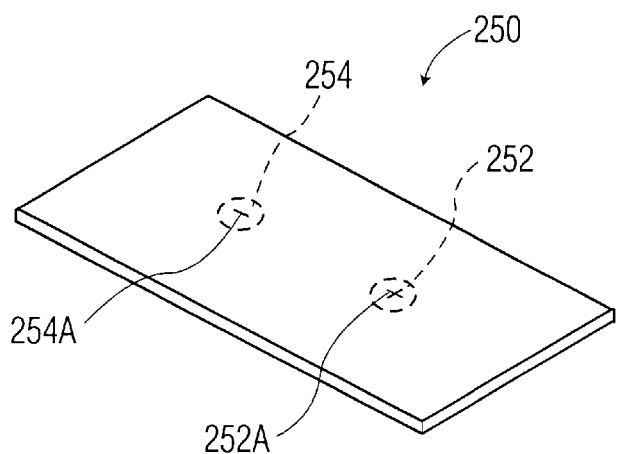
FIG. 5 is a perspective view of an intermediate sheet of a dispenser according to a further embodiment of the present invention.

With reference to FIG. 5, an intermediate sheet 250 as shown therein may be substituted for the intermediate sheet 150 of the dispenser 100. The intermediate sheet 250 includes an entrance membrane 252 and an exit membrane 254 (each indicated by dashed lines) corresponding to the membranes 152 and 154, respectively. The intermediate sheet 250 may be formed in the same manner as the intermediate sheet 150 except that the sheet 250 is further provided with embossments 252A and 254A on the membranes 252 and 254 to control the break pattern of the film. The embossments can be depressions, deformations, scored regions or reduced thickness regions in the film of the sheet 250 and serve to provide preferential release portions or weakened locations.

The embossments 252A and 254A may have different patterns (as shown) or the same pattern. One of the embossments 252A, 254A may be omitted. In particular, the embossment 254A may be omitted in order to provide the membrane 252 with a lower effective burst pressure than the membrane 254. An alternative embossment pattern includes multiple small points which, upon application of a relatively low pressure, will break to convert the selected membrane(s) into a mesh. The embossments 252A, 254A may be formed by any suitable means, for example, by mechanical and/or heat stamping.

Figure 6:
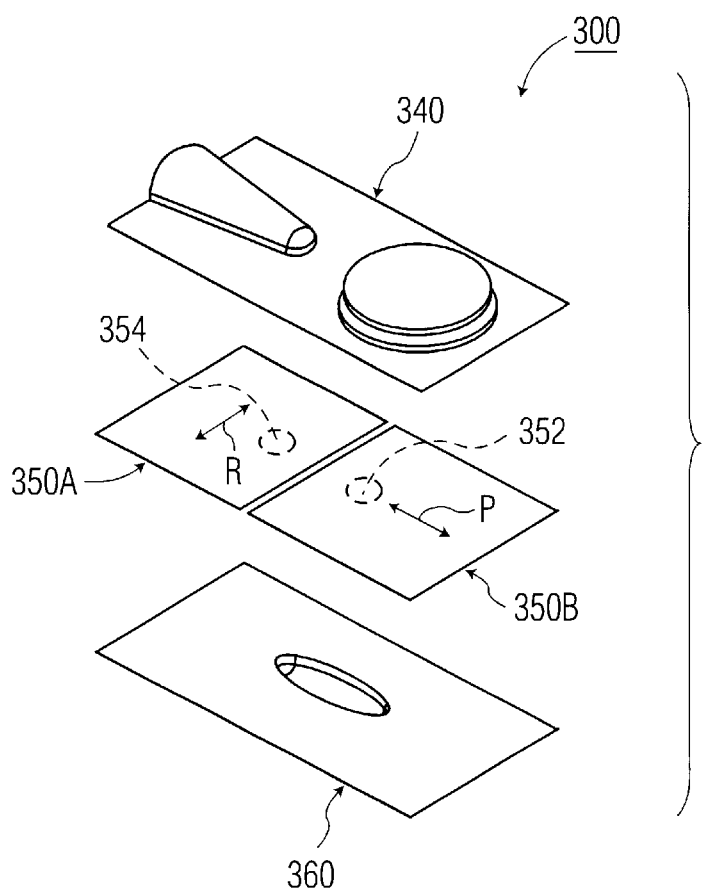
FIG. 6 is an exploded, perspective view of a dispenser according to a further embodiment of the present invention.

With reference to FIG. 6, a dispenser 300 according to a further embodiment is shown therein. The dispenser 300 includes upper and lower sheets 340 and 360 corresponding to the upper and lower sheets 140 and 160, respectively, and can be constructed in the same manner as the dispenser 100 except that the intermediate sheet 150 is replaced with intermediate sheets 350A and 350B. The sheet 350A includes the entrance membrane 352 (indicated by dashed lines) and the sheet 350B includes the exit membrane 354 (indicated by dashed lines). The sheets 350A, 350B are formed of oriented films. As used herein, "oriented film" means a film which is drawn in the direction of flow during or after extrusion. Preferably, the sheets 350A, 350B are formed of uniaxially oriented films.

Preferably, the films of the sheets 350A, 350B are oriented at different angles and, more preferably, at an angle of about 90 degrees with respect to one another. Most preferably, the film of the sheet 350A (and, thus, the film of the entrance membrane 352) is oriented to tear along an axis P substantially parallel to the flow path and the film of the sheet 350B (and, thus, the film of the exit membrane 354) is oriented to tear along an axis R substantially perpendicular to the flow path.

Figure 7:
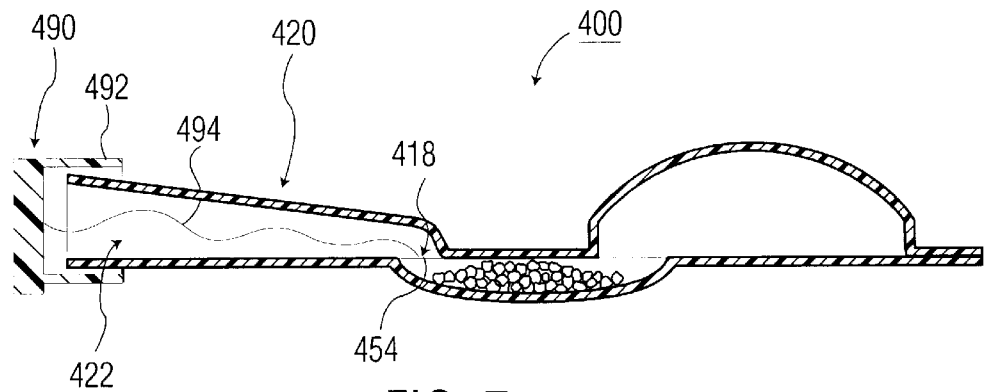
FIG. 7 is a center cross-sectional view of a dispenser according to a further embodiment of the present invention.
Figure 8:
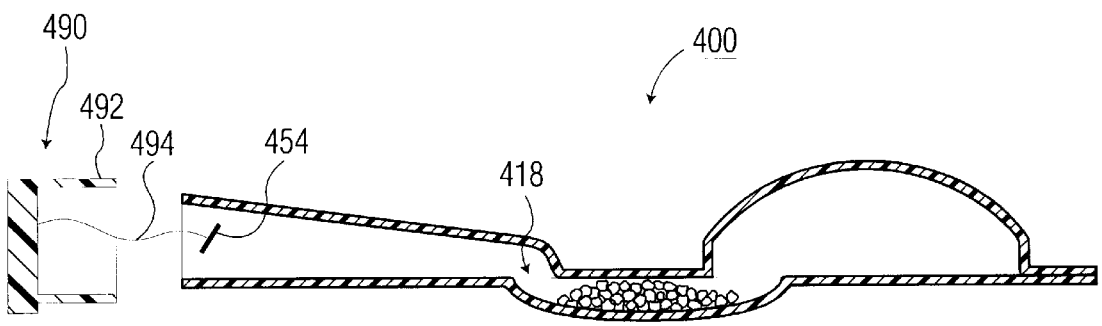
FIG. 8 is a center cross-sectional view of the dispenser of FIG. 7 wherein a cap thereof is removed.

With reference to FIGS. 7 and 8, a dispenser 400 according to a further embodiment of the present invention is shown therein. The dispenser 400 corresponds to the dispenser 100 except that the dispenser 400 is further provided with an end cap assembly 490. The end cap assembly 490 includes a cap 492 that is removably mounted on the diffuser tube 420 as shown in FIG. 7. A connector string 494 is secured to the cap 492, extends through the passage 422, and is secured to the exit membrane 454.

In use, the user first pulls the cap 492 away from the diffuser tube 420, thereby tearing and/or pulling a portion or all of the exit membrane 454 away as shown in FIG. 8. In this manner, the port 418 is partially or fully opened at a desired dispensing time. The user may then actuate the dispenser 400 in the manner described above with regard to the dispenser 100.

Figure 9:
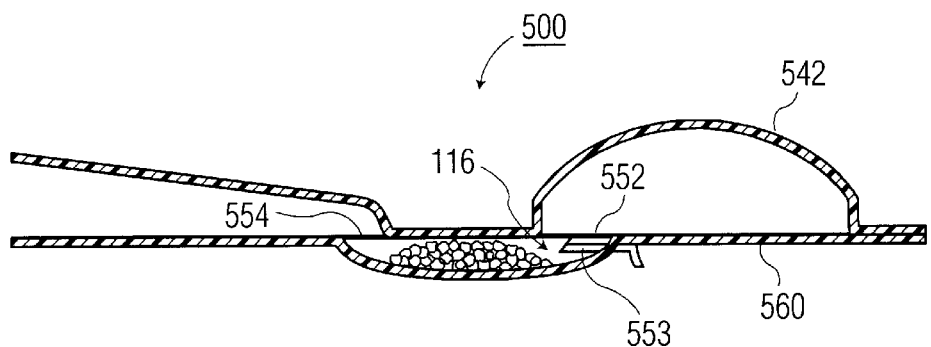
FIG. 9 is a center cross-sectional view of a dispenser according to a further embodiment of the present invention.

With reference to FIG. 9, a dispenser 500 according to further embodiments of the present invention is shown therein. The dispenser 500 corresponds to the dispenser 100 except as follows. A piercing member 553 can be molded into or otherwise secured to the lower sheet 560 (e.g., prior to heat sealing the upper, lower and intermediate sheets). The piercing member 553 extends into the storage volume 116 below the entrance membrane 552.

When the blister 542 is depressed, the pressure therein causes the entrance membrane 552 to deform or bulge downwardly into contact with the piercing member 553. In this manner, the membrane 552 may be pre-pierced or burst at a pressure lower than the pressure required to burst the exit membrane 554.

Figure 10:
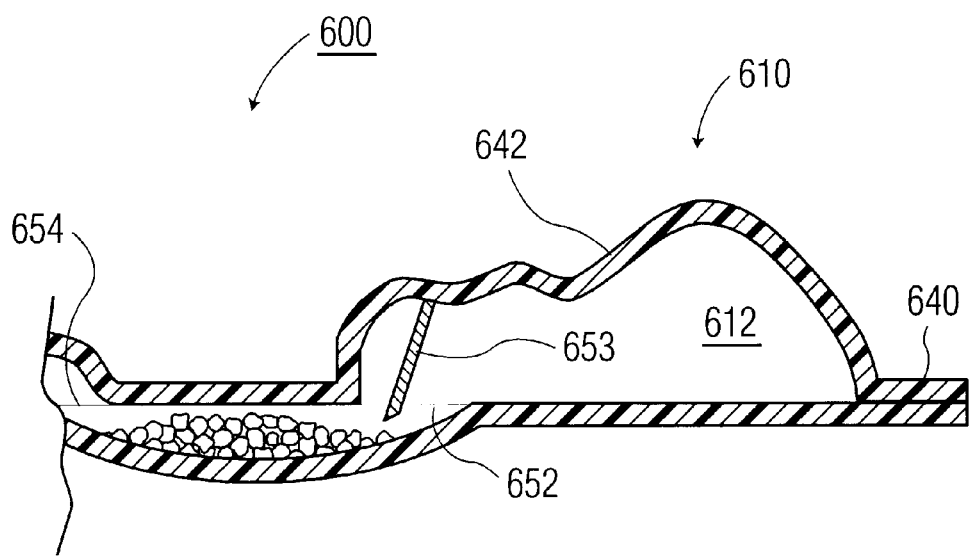
FIG. 10 is a center cross-sectional view of a dispenser according to a further embodiment of the present invention, wherein the dispenser is shown in a partially actuated position.

With reference to FIG. 10, a dispenser 600 according to further embodiments of the present invention is shown therein in a partially actuated position. The dispenser 600 corresponds to the dispenser 100 except as follows. A piercing member 653 is molded into or otherwise secured to the upper sheet 640 and, more particularly, into the blister 642. Prior to actuation of the pressurizing mechanism 610, the piercing member 653 extends downwardly into the gas chamber 612 and is positioned suspended above the entrance membrane 652.

When the blister 642 is depressed, the piercing member 653 is displaced and moves to contact the entrance membrane 652. In this manner, the membrane 652 may be pre-pierced or burst at a pressure lower than the pressure required to burst the exit membrane 654.

Figure 11:
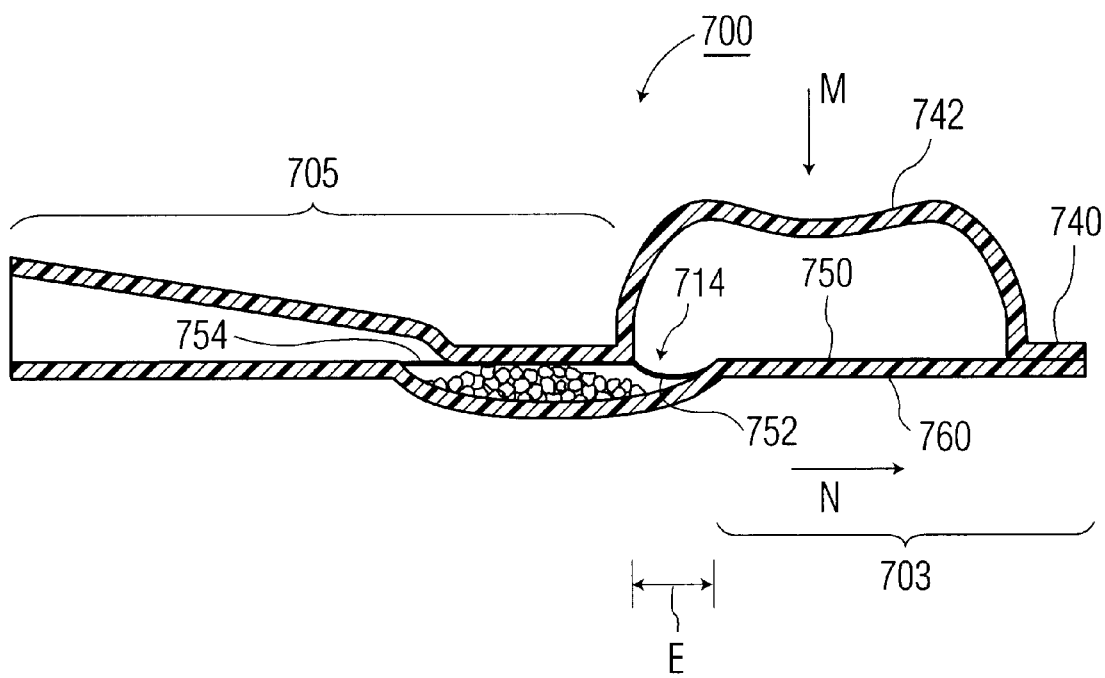
FIG. 11 is a center cross-sectional view of a dispenser according to a further embodiment of the present invention, wherein the dispenser is shown in a partially actuated position.

With reference to FIG. 11, a dispenser 700 according to further embodiments is shown therein in a partially actuated position. The dispenser 700 corresponds to the dispenser 100 except as follows. The stiffness, elasticity and other appropriate characteristics of the upper sheet 740, the lower sheet 760 and the intermediate sheet 750 are selected such that, as the blister 742 is depressed in a direction M, the portions of the several sheets 740, 750, 760 upstream of the entrance port 714 (collectively, the dispenser portion 703) stretch laterally in the direction N relative to the portions of the sheets 740, 750, 760 downstream of the entrance port 714 (collectively, the dispenser portion 705). This stretching increases the length E of the port along the direction N (i.e., substantially along the length of the flow path) and thereby distorts the entrance membrane 752. Such distortion creates non-uniformity in the entrance membrane 752 and resultant stress concentrations. In this manner, the entrance membrane 752 may be burst at a pressure lower than the pressure required to burst the exit membrane 754.

Figure 12:
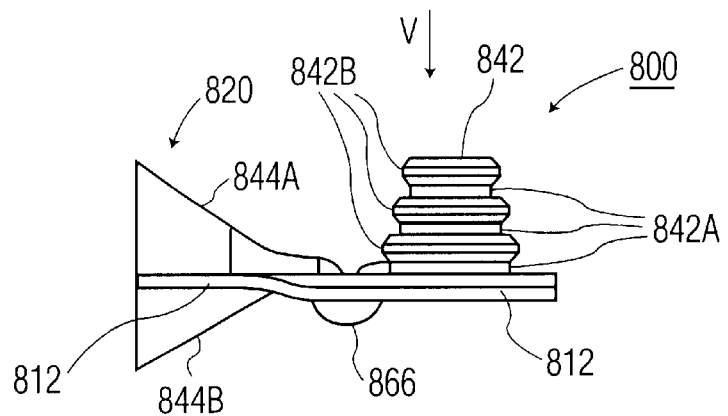
FIG. 12 is a side elevational view of a dispenser according to a further embodiment of the present invention.
Figure 13:
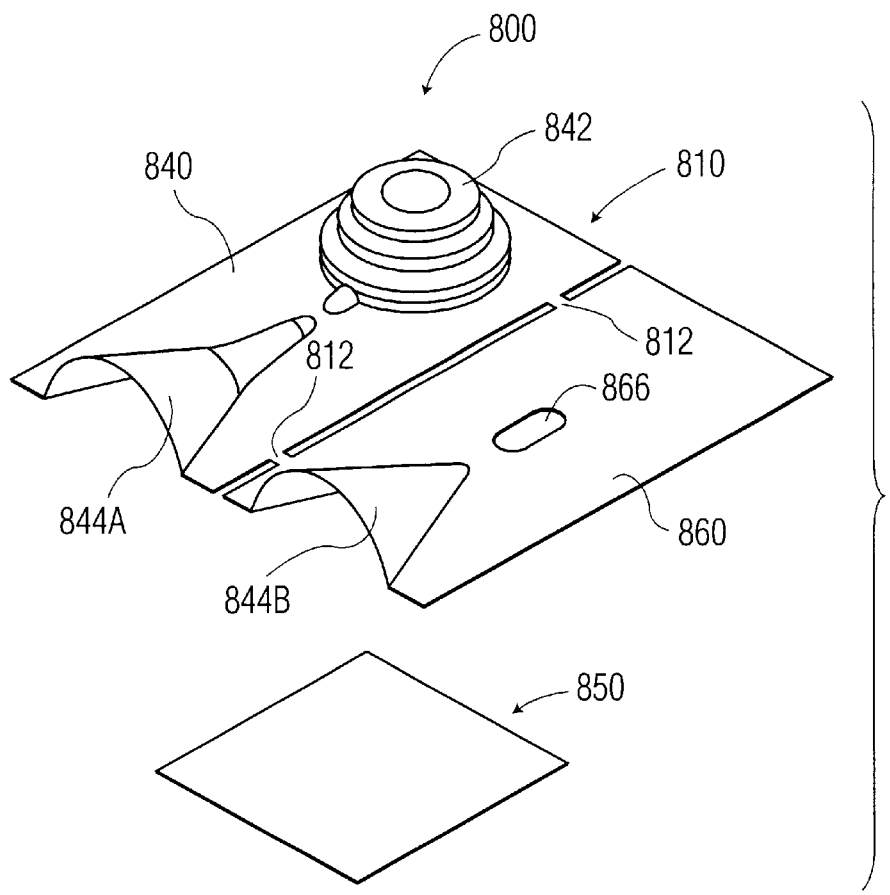
FIG. 13 is an exploded, perspective view of the dispenser of FIG. 12 prior to assembly.

With reference to FIGS. 12 and 13, a dispenser 800 according to further embodiments of the present invention is shown therein. The dispenser 800 has an upper sheet 840, an intermediate sheet 850 and a lower sheet 860 corresponding to the sheets 140, 150 and 160, respectively, except as follows.

The upper sheet 840 and the lower sheet 860 are integrally formed as a clam shell member 810 and are pivotably joined by hinge portions 812. Cone shaped diffuser channels 844A and 844B are formed in the sheets 840 and 860, respectively. To assemble the dispenser 800, the sheets 840, 860 are folded or pivoted about the hinges 812 with the sheet 850 positioned therebetween. The channels 844A, 844B combine to form an enlarged conical diffuser tube 820. Optionally, the channel 844B may be replaced with a planar portion as is the dispenser 100.

The dispenser 800 has a generally accordion or bellows shaped blister 842. The blister 842 has generally vertically extending ring shaped walls 842A and ring shaped, rounded connecting walls 842B. The walls 842A are preferably substantially concentric with each other and with the walls 842B. The blister 842 is tapered such that the diameters of the walls 842A, 842B decrease incrementally toward the upper end of the blister 842.

When the blister 842 is depressed, the walls 842 tend to guide the blister 842 in a vertical direction V which is preferably collinear with the common central axis of the walls 842A, 842B. The rounded walls 842B allow the blister 842 to collapse easily against the underlying segments. The telescoping shape of the blister 842 helps to prevent rollover of the blister as it is being depressed.

Figure 14:
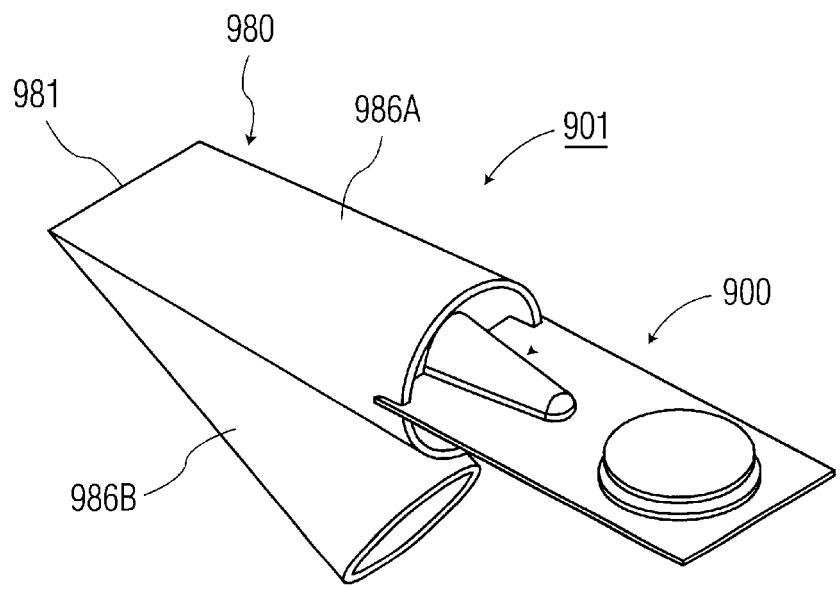
FIG. 14 is a perspective view of a delivery device according to a further embodiment of the present invention, wherein a delivery tube thereof is in a folded position.
Figure 15:
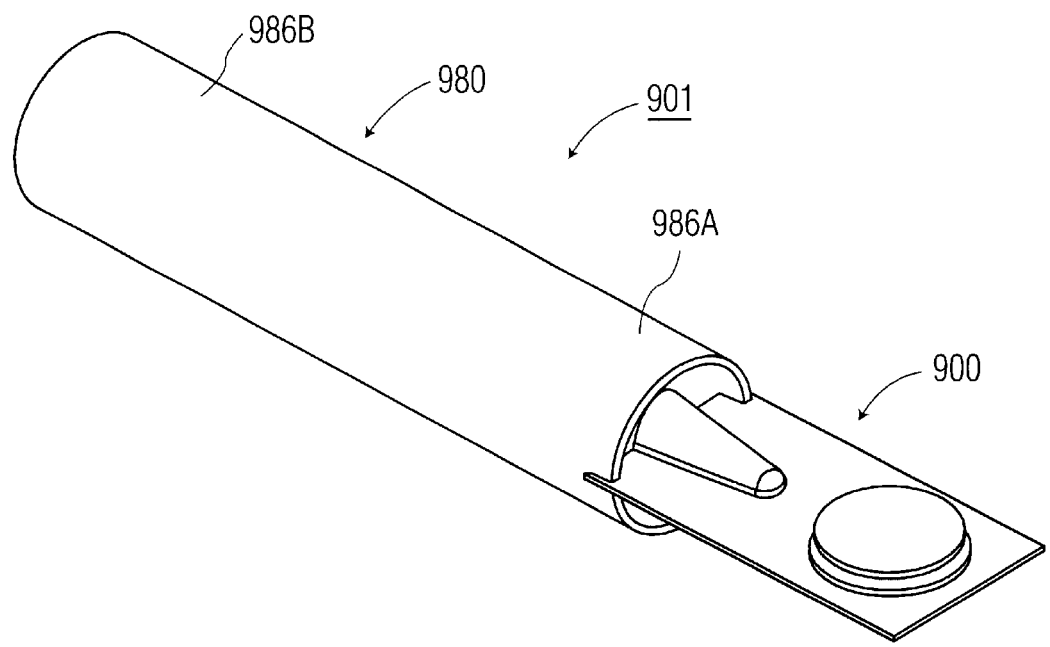
FIG. 15 is a perspective view of the delivery device of FIG. 15, wherein the delivery tube thereof is shown in an extended, operative position.

With reference to FIGS. 14 and 15, a delivery device 901 according to further embodiments of the present invention is shown therein. The delivery device 901 includes a delivery tube 980 and a dispenser 900 corresponding to the dispenser 100. The delivery tube 980 is configured and formed of a suitable material such that the delivery tube 980 is foldable. Suitable materials may include polystyrene, polyvinyl chloride (PVC), polypropylene, polyethylene, polyester or ABS. The delivery tube 980 may be maintained in a folded position, as shown in FIG. 14, such that portions 986A and 986B of the delivery tube 980 are joined along a fold 981. This position may be particularly advantageous for storing the delivery device 901. When the user wishes to administer a dose from the dispenser 900, the user may unfold the portion 986B about the fold 981 to extend the delivery tube 980 in the delivery position as shown in FIG. 15.

Figure 16:
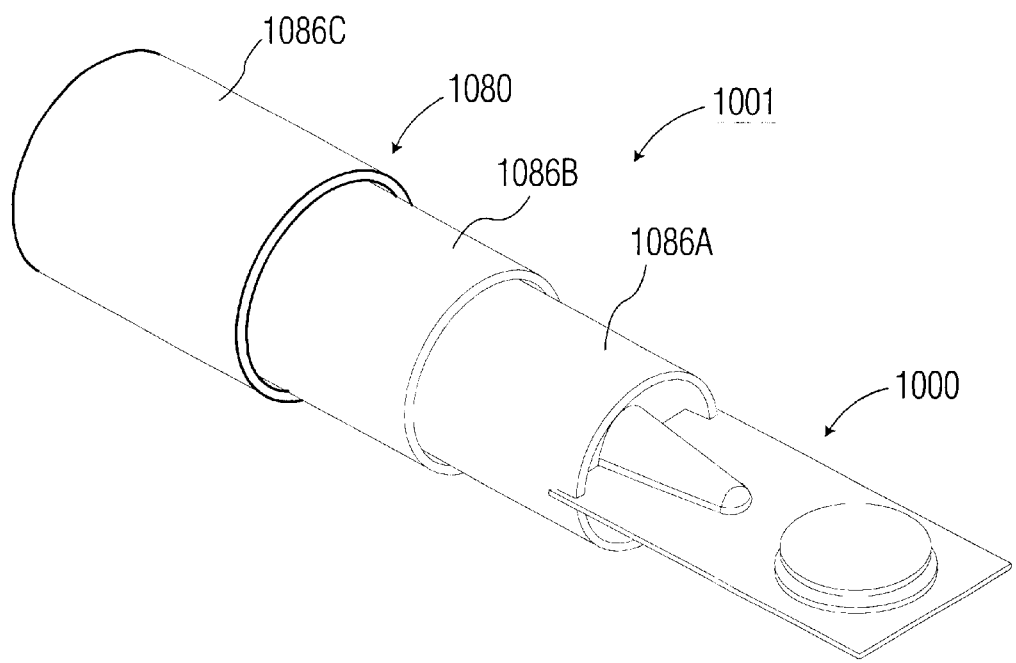
FIG. 16 is a perspective view of a delivery device according to a further embodiment of the present invention, wherein a delivery tube thereof is shown in an extended position.
Figure 17:
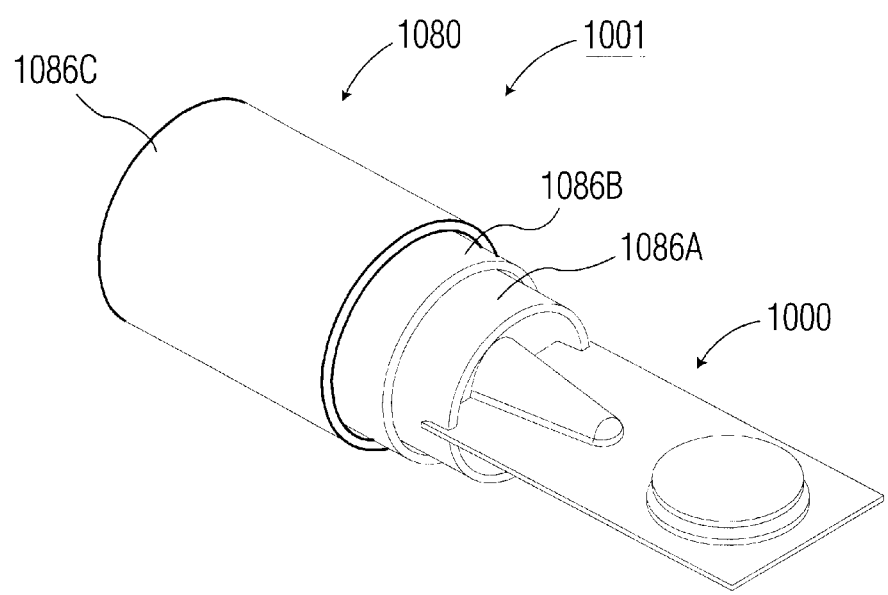
FIG. 17 is a perspective view of the delivery device of FIG. 16, wherein the delivery tube thereof is shown in a retracted position.

With reference to FIGS. 16 and 17, a delivery device 1001 according to further embodiments of the present invention is shown therein. The delivery device 1001 includes a dispenser 1000 corresponding to the dispenser 100. The delivery device 1001 further includes a delivery tube 1080. The delivery tube 1080 includes a plurality of telescoping segments 1086A, 1086B, 1086C. For storage, the delivery tube 1080 may be slidably nested or compressed as shown in FIG. 17. The delivery tube 1080 may thereafter be re-extended as shown in FIG. 16 for use.

Figure 18:
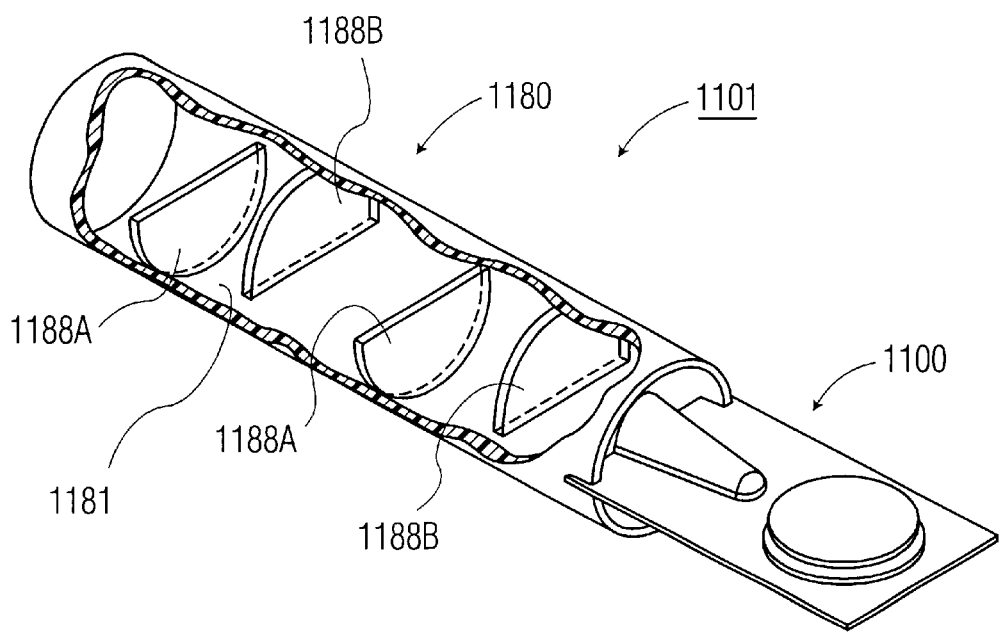
FIG. 18 is a perspective, fragmentary view of a delivery device according to a further embodiment of the present invention.

With reference to FIG. 18, a delivery device 1101 according to further embodiments of the present invention is shown therein. The delivery device 1101 includes a dispenser 1100 corresponding to the dispenser 100. The delivery device 1101 further includes a delivery tube 1180. The delivery tube 1180 corresponds to the delivery tube 180 except that a plurality of baffles 1188A and 1188B are secured to the interior surface 1181 of the delivery tube 1180 and extend radially inwardly therefrom. The baffles 1188A, 1188B are preferably integrally molded into the delivery tube 1180. The baffles 1188A and the baffles 1188B extend from opposing sides of the delivery tube 1180 and are arranged in a sequentially alternating fashion. The baffles 1188A, 1188B may serve to slow the plume of medicament from the dispenser 1100. The baffles 1188A, 1188B may also serve to deaggregate the medicament and also to induce additional turbulence in the carrier gas stream to aid in mixing of the medicament with the carrier gas stream.

Figure 19:
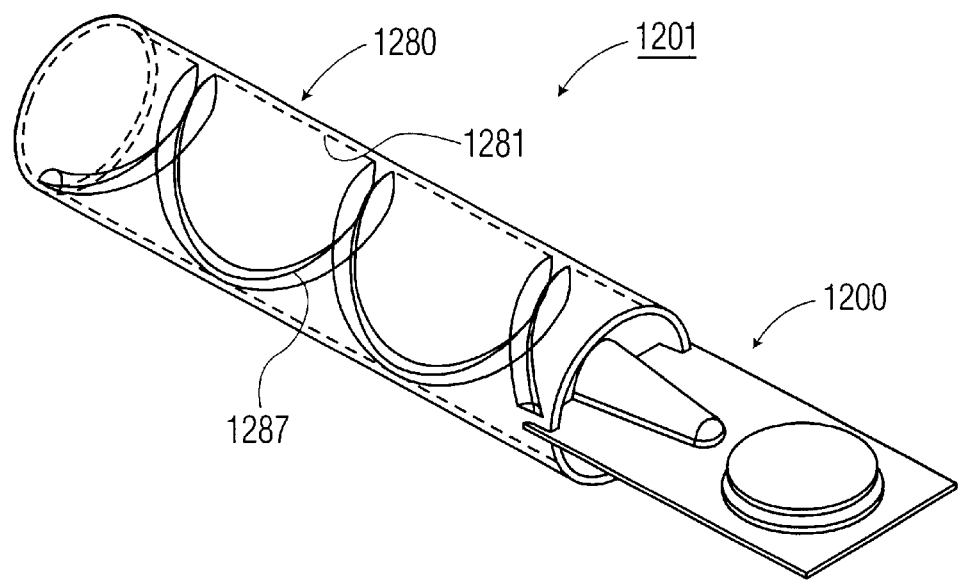
FIG. 19 is a perspective, schematic view of a delivery device according to a further embodiment of the present invention.

With reference to FIG. 19, a delivery device 1201 according to further embodiments of the present invention is shown therein. The delivery device 1201 includes a dispenser 1200 corresponding to the dispenser 100. The delivery device 1201 further includes a delivery tube 1280. A helical rib 1287 is secured to and extends radially inwardly from the interior surface 1281 of the delivery tube 1280. The rib can be integrally molded with the delivery tube 1280. The helical rib 1287 extends down at least a portion of the length of the interior wall of the delivery tube 1280. Preferably, the rib 1287 has a radially extending height of between about ⅕ and ⅘ of the exit tube diameter. The helical rib 1287 may serve the functions discussed above with regard to the baffles 1188A, 1188B.

Figure 20:
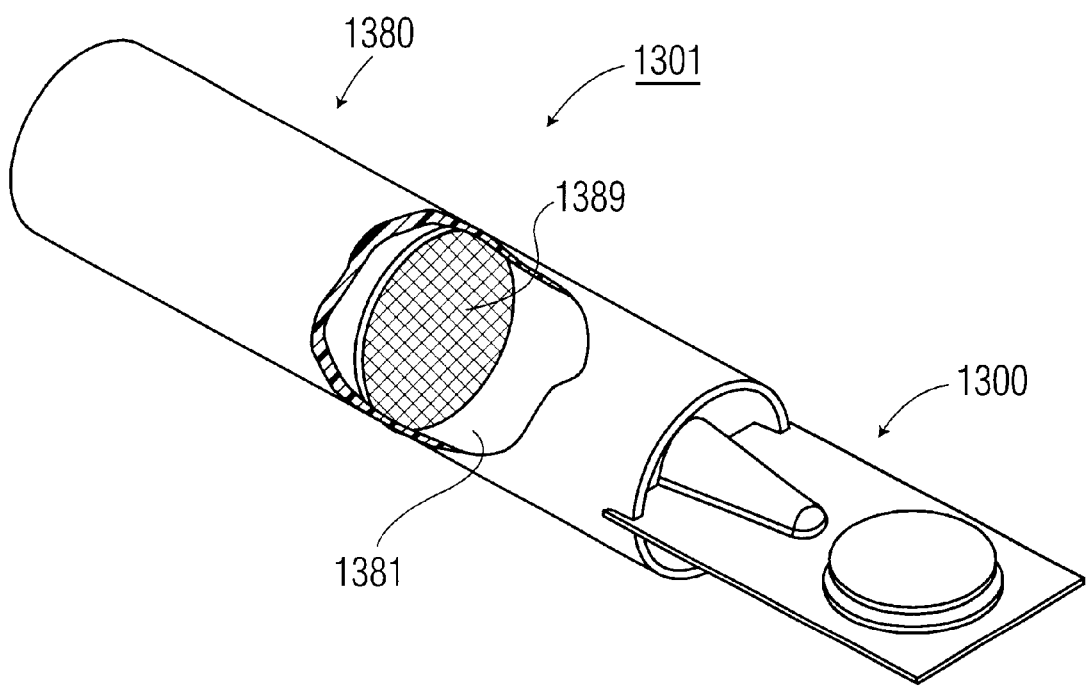
FIG. 20 is a perspective, fragmentary view of a delivery device according to a further embodiment of the present invention.

With reference to FIG. 20, a delivery device 1301 according to further embodiments of the present invention is shown therein. The delivery device 1301 includes a dispenser 1300 corresponding to the dispenser 100, for example. The delivery device 1301 further includes a delivery tube 1380 corresponding to the delivery tube 180 except as follows. A mesh or screen 1389 is positioned in and secured to the interior surface 1381 of the delivery tube 1380. Preferably, the screen 1389 extends fully across the width of the delivery tube 1380. The preferred mesh size of the screen 1389 will depend on the optimum particle size of the powder to be delivered. The screen 1389 is preferably formed of a plastic material. The screen 1389 may serve the functions discussed above with regard to the baffles 1188A, 1188B.

As a further alternative, baffles corresponding to the baffles 1188A, 1188B may be secured to and extend radially inwardly from the interior wall or the delivery opening 124 of the diffuser tube 120, for example. Similarly, a helical rib corresponding to the helical rib 1287 may be provided in the diffuser tube 120, for example. Also, as a further alternative, a screen corresponding to the screen 1389 may be mounted in the diffuser tube 120 or the port 124.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A medicament delivery device for administering an inhalable medicament to a user, said device comprising:
   a) a medicament reservoir;
   b) an entrance port and an exit port each disposed adjacent said reservoir;
   c) a gas chamber disposed adjacent said entrance port;
   d) a pressurizing mechanism operable to pressurize said gas chamber to at least a prescribed pressure;
   e) a first frangible membrane extending across said entrance port and separating said reservoir from said gas chamber;
   f) a second frangible membrane extending across said exit port; and g) a tube disposed adjacent said exit port and defining a delivery opening opposite said exit port, said delivery opening being open prior to actuation of said pressurizing mechanism;

h) wherein, when said pressurizing mechanism is actuated, at least one of said first and second membranes is responsive to said prescribed pressure in said gas chamber to burst to allow gas to flow through said entrance port and said reservoir and to carry the medicament through said exit port.

2. The medicament delivery device of claim 1 wherein each of said first and second membranes is responsive to said prescribed pressure in said gas chamber to burst.

3. The medicament delivery device of claim 1 wherein said medicament delivery device is configured to rupture said first membrane when a pressure less than said prescribed pressure is present in said gas chamber and, when said pressurizing mechanism is actuated, said second membrane is responsive to said prescribed pressure in said gas chamber to burst.

4. The medicament delivery device of claim 1 wherein said tube is a diffuser tube.

5. The medicament delivery device of claim 1 including at least one impaction structure disposed between said reservoir and said delivery opening.

6. The medicament delivery device of claim 5 wherein said impaction structure includes a baffle.

7. The medicament delivery device of claim 5 wherein said impaction structure includes a screen.

8. The medicament delivery device of claim 1 including a weakening embossment formed in at least one of said first and second membranes.

9. The medicament delivery device of claim 1 wherein at least one of said first and second membranes is an oriented film.

10. The medicament delivery device of claim 9 wherein each of said first and second membranes is an oriented film and said first and second membranes are oriented at different angles.

11. The medicament delivery device of claim 1 including a removable end cap configured to rupture at least one of said first and second membranes upon removal of said end cap from said medicament delivery device.

12. The medicament delivery device of claim 1 including a piercing member operative to engage and tear said first membrane when said pressurizing mechanism is actuated.

13. The medicament delivery device of claim 12 wherein said piercing member is configured to engage said first membrane on a surface of said first membrane facing said reservoir.

14. The medicament delivery device of claim 12 wherein said piercing member is configured to engage said first membrane on a surface of said first membrane facing said gas chamber.

15. The medicament delivery device of claim 1 wherein said at least one of said first and second membranes has a burst pressure of between about 4.4 and 89.0 Newtons.

16. The medicament delivery device of claim 1 wherein said at least one of said first and second membranes has a tensile strength of between about 10 and 50 MPascals.

17. The medicament delivery device of claim 1 including a delivery tube communicating with said tube.

18. The medicament delivery device of claim 17 wherein said delivery tube is foldable.

19. The medicament delivery device of claim 17 wherein said delivery tube includes a plurality of telescoping portions.

20. The medicament delivery device of claim 17 wherein said delivery tube includes an inner surface and at least one baffle extending radially inwardly from said inner surface.

21. The medicament delivery device of claim 17 wherein said delivery tube includes an inner surface and at least one helical rib extending inwardly from said inner surface.

22. The medicament delivery device of claim 17 wherein said delivery tube includes a screen mounted therein.

23. The medicament delivery device of claim 1 including a medicament disposed in said reservoir.

24. The medicament delivery device of claim 23 wherein said medicament is a dry powder.

25. The medicament delivery device of claim 1 wherein said pressurizing mechanism includes a compressible blister defining said gas chamber and operable to pressurize said gas chamber to at least said prescribed pressure.

26. The medicament delivery device of claim 25 comprising:

a) a first sheet including said compressible blister formed therein;

b) a second sheet defining said reservoir therein; and c) an intermediate layer disposed between said first and second sheets, said first and second membranes forming a part of said intermediate layer.

27. The medicament delivery device of claim 26 wherein each of said first and second sheets is thermoformed.

28. The medicament delivery device of claim 26 wherein said tube is integral with at least one of said first and second sheets.

29. The medicament delivery device of claim 25 including a piercing member secured to said blister and disposed in said gas chamber, wherein, when said blister is compressed, said piercing member engages said first membrane.

30. The medicament delivery device of claim 25 wherein, when said blister is compressed, the size of said entrance port increases to distort said first membrane.

31. The medicament delivery device of claim 25 wherein said blister is bellowed.

32. The medicament delivery device of claim 25 wherein said gas chamber has a volume of between about 0.2 and 10 milliliters.

33. A medicament delivery device for administering an inhalable medicament to a user, said device comprising:

a) a medicament reservoir;

b) an entrance port and an exit port each disposed adjacent said reservoir;

c) a compressible blister defining a gas chamber and operable to pressurize said gas chamber to at least a prescribed pressure;

d) a frangible membrane extending across said entrance port and separating said reservoir from said gas chamber; and e) a tube disposed adjacent said exit port and defining a delivery opening opposite said exit port, said delivery opening being open prior to compression of said blister;

f) wherein, when said blister is compressed, said membrane is responsive to said prescribed pressure in said gas chamber to burst to allow gas to flow through said entrance port and said reservoir and to carry the medicament through said exit port.

34. A method for administering an inhalable medicament to a user, said method comprising the steps of:

a) providing a medicament delivery device including:

1) a medicament reservoir;

2) an entrance port and an exit port each disposed adjacent the reservoir;

3) a gas chamber disposed adjacent the entrance port;
4) a pressurizing mechanism operable to pressurize the gas chamber to at least a prescribed pressure;
5) a first frangible membrane extending across the entrance port and separating the reservoir from the gas chamber; and
6) a second frangible membrane extending across the exit port; and b) actuating the pressurizing mechanism to generate the prescribed pressure in the gas chamber, whereupon at least one of the first and second membranes bursts to allow gas to flow through the entrance port and the reservoir and to carry the medicament through the exit port.

35. A method for administering an inhalable medicament to a user, said method comprising the steps of:
a) providing a medicament delivery device including:
1) a medicament reservoir;
2) an entrance port and an exit port each disposed adjacent the reservoir;
3) a compressible blister defining a gas chamber and operable to pressurize the gas chamber to at least a prescribed pressure; and
4) a frangible membrane extending across the entrance port and separating the reservoir from the gas chamber; and b) compressing the blister to generate the prescribed pressure in the gas chamber, whereupon the frangible membrane bursts to allow gas to flow through the entrance port and the reservoir and to carry the medicament through the exit port.

36. A medicament delivery device for administering an inhalable medicament to a user, comprising:
a medicament reservoir, an inlet port communicating with said medicament reservoir, an outlet port communicating with said medicament reservoir, a tube disposed adjacent said outlet port and defining a delivery opening opposite said outlet port, and a thin polymeric burstable membrane located between said outlet port and said medicament reservoir sealing said outlet port, said delivery opening being open prior to said thin polymeric burstable membrane being burst, whereby fluid pressure delivered to said reservoir will burst said thin polymeric burstable membrane, fluidize medicament contained in said medicament reservoir and deliver fluidized medicament to said outlet port.

37. The medicament delivery device defined in claim 36, wherein said thin polymeric burstable membrane is formed of polyurethane having a thickness of between 0.5 and 4 mils.

38. The medicament delivery device defined in claim 36, wherein said thin polymeric burstable membrane is a uniaxially oriented polyethylene film.

39. The medicament delivery device defined in claim 36, wherein said medicament reservoir includes powdered medicament.

40. The medicament delivery device defined in claim 36, wherein said medicament delivery device includes a thin polymeric film located between said inlet port and said medicament reservoir sealing said inlet port and said medicament reservoir.

41. The medicament delivery device defined in claim 40, wherein said thin polymeric film comprises a thin polymeric burstable film having a thickness of between 0.5 and 4 mils, whereby fluid pressure delivered to said inlet port substantially simultaneously bursts said thin polymeric burstable film sealing said inlet port and said thin burstable polymeric membrane sealing said outlet port.

42. The medicament delivery device defined in claim 40, wherein said thin polymeric film and said thin polymeric burstable membrane are formed from a single sheet of polyethylene.

43. The medicament delivery device defined in claim 40, wherein said thin polymeric film and said thin polymeric burstable membrane are formed of uniaxially oriented film.

44. The medicament delivery device defined in claim 43, wherein said thin polymeric film and said thin polymeric burstable membrane are formed of uniaxially oriented films oriented at different angles.

45. The medicament delivery device defined in claim 43, wherein said thin polymeric burstable membrane and said thin polymeric film are uniaxially oriented films oriented at approximately 90 degrees relative to one another.

46. The medicament delivery device defined in claim 41, wherein said medicament delivery device includes a piercing element adapted to pierce said thin polymeric film upon delivery of fluid pressure to said medicament reservoir.

47. The medicament delivery device defined in claim 41, wherein said medicament delivery device includes a piercing member and a pressurizing mechanism operable to deliver pressure to said thin polymeric film and substantially simultaneously activate said piercing member to pierce said thin polymeric film.

* * * * *